(12) United States Patent  
Gilbert et al.

(10) Patent No.: US 8,945,115 B2  
(45) Date of Patent: Feb. 3, 2015

(54) SYSTEM AND METHOD FOR POWER SUPPLY NOISE REDUCTION

(71) Applicant: Covidien LP, Mansfield, MA (US)

(72) Inventors: James A. Gilbert, Boulder, CO (US); Calvin S. Bromfield, Jr., Englewood, CO (US)

(73) Assignee: Covidien LP, Mansfield, MA (US)

( * ) Notice: Subject to any disclaimer, the term of this patent is extended or adjusted under 35 U.S.C. 154(b) by 172 days.

(21) Appl. No.: 13/777,234

(22) Filed: Feb. 26, 2013

(65) Prior Publication Data

US 2013/0178848 A1 Jul. 11, 2013

Related U.S. Application Data

(62) Division of application No. 12/556,770, filed on Sep. 10, 2009, now Pat. No. 8,382,751.

(51) Int. Cl.
*A61B 18/12* (2006.01)

(52) U.S. Cl.
CPC .................................. *A61B 18/1206* (2013.01)
USPC .............................................. 606/38; 606/34

(58) Field of Classification Search
USPC ..................................................... 606/34–38
See application file for complete search history.

(56) References Cited

U.S. PATENT DOCUMENTS

| 3,697,808 A | 10/1972 | Lee |
| 3,952,748 A | 4/1976 | Kaliher et al. |
| 4,569,345 A | 2/1986 | Manes |
| 4,586,120 A | 4/1986 | Mailk et al. |
| 4,651,264 A | 3/1987 | Shiao-Chung Hu |
| 4,788,634 A | 11/1988 | Schlecht et al. |
| 4,887,199 A | 12/1989 | Whittle |
| 5,099,840 A | 3/1992 | Goble et al. |
| 5,119,284 A | 6/1992 | Fisher et al. |
| 5,304,917 A | 4/1994 | Somerville |

(Continued)

FOREIGN PATENT DOCUMENTS

| DE | 179607 | 3/1905 |
| DE | 1099658 | 2/1961 |

(Continued)

OTHER PUBLICATIONS

U.S. Appl. No. 10/406,690, filed Apr. 3, 2003.

(Continued)

*Primary Examiner* — Jaymi Della

(57) ABSTRACT

An electrosurgical system includes an electrosurgical generator, a power source configured to deliver power to at least one load connected to the generator, a master configured to generate an initial pulse, the initial pulse cooperating with a first floating power supply configured to create an electrical connection between at least one first load and the power source, and a plurality of slaves connected in series to the master, wherein a first slave is configured to generate a subsequent pulse based on the initial pulse, the subsequent pulse cooperating with a second floating power supply configured to create an electrical connection between at least one second load and the power source, the subsequent pulse configured to cause an ensuing slave to generate an additional pulse, the additional pulse cooperating with a corresponding floating power supply configured to create an electrical connection between at least one additional load and the power source.

9 Claims, 4 Drawing Sheets

(56) References Cited

U.S. PATENT DOCUMENTS

| | | | |
|---|---|---|---|
| 5,438,302 A | 8/1995 | Goble | |
| 5,694,304 A | 12/1997 | Telefus et al. | |
| 5,712,772 A | 1/1998 | Telefus et al. | |
| 5,729,448 A | 3/1998 | Haynie et al. | |
| 6,142,992 A | 11/2000 | Cheng et al. | |
| 6,188,211 B1 | 2/2001 | Rincon-Mora et al. | |
| 6,200,314 B1 | 3/2001 | Sherman | |
| 6,296,636 B1 | 10/2001 | Cheng et al. | |
| 6,426,886 B1 | 7/2002 | Goder | |
| 6,620,157 B1 | 9/2003 | Dabney et al. | |
| 7,175,618 B2 | 2/2007 | Dabney et al. | |
| 7,422,582 B2 | 9/2008 | Malackowski et al. | |

FOREIGN PATENT DOCUMENTS

| | | |
|---|---|---|
| DE | 1139927 | 11/1962 |
| DE | 1149832 | 6/1963 |
| DE | 1439302 | 1/1969 |
| DE | 2439587 | 2/1975 |
| DE | 2455174 | 5/1975 |
| DE | 2407559 | 8/1975 |
| DE | 2602517 | 7/1976 |
| DE | 2504280 | 8/1976 |
| DE | 2540968 | 3/1977 |
| DE | 2820908 | 11/1978 |
| DE | 2803275 | 8/1979 |
| DE | 2823291 | 11/1979 |
| DE | 2946728 | 5/1981 |
| DE | 3143421 | 5/1982 |
| DE | 3045996 | 7/1982 |
| DE | 3120102 | 12/1982 |
| DE | 3510586 | 10/1986 |
| DE | 3604823 | 8/1987 |
| DE | 390937 | 4/1989 |
| DE | 3904558 | 8/1990 |
| DE | 3942998 | 7/1991 |
| DE | 4339049 | 5/1995 |
| DE | 19717411 | 11/1998 |
| DE | 19848540 | 5/2000 |
| EP | 246350 | 11/1987 |
| EP | 310431 | 4/1989 |
| EP | 325456 | 7/1989 |
| EP | 0325456 | 7/1989 |
| EP | 336742 | 10/1989 |
| EP | 390937 | 10/1990 |
| EP | 556705 | 8/1993 |
| EP | 608609 | 8/1994 |
| EP | 836868 | 4/1998 |
| EP | 1051948 | 11/2000 |
| EP | 880220 | 6/2006 |
| FR | 1275415 | 10/1961 |
| FR | 1347865 | 11/1963 |
| FR | 2313708 | 12/1976 |
| FR | 2364461 | 7/1978 |
| FR | 2502935 | 10/1982 |
| FR | 2517953 | 6/1983 |
| FR | 2573301 | 5/1986 |
| SU | 166452 | 1/1965 |
| SU | 727201 | 4/1980 |
| WO | WO02/11634 | 2/2002 |
| WO | WO02/45589 | 6/2002 |
| WO | WO02/053048 | 7/2002 |
| WO | WO03/090635 | 11/2003 |
| WO | WO2006/050888 | 5/2006 |

OTHER PUBLICATIONS

U.S. Appl. No. 10/573,713, filed Mar. 28, 2006.
U.S. Appl. No. 11/242,458, filed Oct. 3, 2005.
U.S. Appl. No. 12/136,620, filed Jun. 10, 2008.
U.S. Appl. No. 12/184,556, filed Aug. 1, 2008.
U.S. Appl. No. 12/203,734, filed Sep. 3, 2008.
U.S. Appl. No. 12/205,298, filed Sep. 5, 2008.
U.S. Appl. No. 12/205,525, filed Sep. 5, 2008.
U.S. Appl. No. 12/241,861, filed Sep. 30, 2008.
U.S. Appl. No. 12/241,905, filed Sep. 30, 2008.
U.S. Appl. No. 12/241,942, filed Sep. 30, 2008.
U.S. Appl. No. 12/241,983, filed Sep. 30, 2008.
U.S. Appl. No. 12/242,026, filed Sep. 30, 2008.
U.S. Appl. No. 12/242,061, filed Sep. 30, 2008.
U.S. Appl. No. 12/242,102, filed Sep. 30, 2008.
U.S. Appl. No. 12/249,218, filed Oct. 10, 2008.
U.S. Appl. No. 12/249,263, filed Oct. 10, 2008.
U.S. Appl. No. 12/351,935, filed Jan. 12, 2009.
U.S. Appl. No. 12/351,947, filed Jan. 12, 2009.
U.S. Appl. No. 12/351,960, filed Jan. 12, 2009.
U.S. Appl. No. 12/351,970, filed Jan. 12, 2009.
U.S. Appl. No. 12/351,980, filed Jan. 12, 2009.
U.S. Appl. No. 12/353,002, filed Jan. 13, 2009.
U.S. Appl. No. 12/353,012, filed Jan. 13, 2009.
U.S. Appl. No. 12/407,896, filed Mar. 20, 2009.
U.S. Appl. No. 12/477,245, filed Jun. 3, 2009.
U.S. Appl. No. 12/481,087, filed Jun. 9, 2009.
U.S. Appl. No. 12/534,308, filed Aug. 3, 2009.
U.S. Appl. No. 12/540,190, filed Aug. 12, 2009.
U.S. Appl. No. 12/549,563, filed Aug. 28, 2009.
U.S. Appl. No. 12/556,770, filed Sep. 10, 2009.
U.S. Appl. No. 12/566,173, filed Sep. 24, 2009.
U.S. Appl. No. 12/566,233, filed Sep. 24, 2009.
U.S. Appl. No. 12/567,966, filed Sep. 28, 2009.
U.S. Appl. No. 12/613,876, filed Nov. 6, 2009.
Wald et al., "Accidental Burns", JAMA, Aug. 16, 1971, vol. 217, No. 7, pp. 916-921.
Vallfors et al., "Automatically Controlled Bipolar Electrosoagulation—'COA-COMP'" Neurosurgical Review 7:2-3 (1984) pp. 187-219.
Sugita et al., "Bipolar Coagulator with Automatic Thermocontrol" J. Neurosurg., vol. 41, Dec. 1944., pp. 777-779.
Muller et al. "Extended Left Hemicolectomy Using the LigaSure Vessel Sealing System" Innovations That Work; Company Newsletter; Sep. 1999.
Ogden Goertzel Alternative to the Fourier Transform: Jun. 1993 pp. 485-487 Electronics World; Reed Business Publishing, Sutton, Surrey, BG vol. 99, No. 9. 1687.
Hadley I C D et al., "Inexpensive Digital Thermometer for Measurements on Semiconductors" International Journal of Electronics; Taylor and Francis. Ltd.; London, GB; vol. 70, No. 6 Jun. 1, 1991; pp. 1155-1162.
Richard Wolf Medical Instruments Corp. Brochure, "Kleppinger Bipolar Forceps & Bipolar Generator" 3 pp. Jan. 1989.
Astrahan, "A Localized Current Field Hyperthermia System for Use with 192-Iridium Interstitial Implants" Medical Physics, 9 (3), May/Jun. 1982.
Alexander et al., "Magnetic Resonance Image-Directed Stereotactic Neurosurgery: Use of Image Fusion with Computerized Tomography to Enhance Spatial Accuracy" Journal Neurosurgery, 83; (1995) pp. 271-276.
Geddes et al., "The Measurement of Physiologic Events by Electrical Impedance" Am. J. MI, Jan. Mar. 1964, pp. 16-27.
Cosman et al., "Methods of Making Nervous System Lesions" In William RH, Rengachary SS (eds): Neurosurgery, New York: McGraw-Hill, vol. 111, (1984), pp. 2490-2499.
Anderson et al., "A Numerical Study of Rapid Heating for High Temperature Radio Frequency Hyperthermia" International Journal of Bio-Medical Computing, 35 (1994) pp. 297-307.
Cosman et al., "Radiofrequency Lesion Generation and Its Effect on Tissue Impedance" Applied Neurophysiology 51: (1988) pp. 230-242.
Ni W. et al. "A Signal Processing Method for the Coriolis Mass Flowmeter Based on a Normalized . . . " Journal of Applied Sciences—Yingyong Kexue Xuebao, Shangha CN, vol. 23 No. 2;(Mar. 2005); pp. 160-164.
Chicharo et al. "A Sliding Goertzel Algoritm" Aug. 1996, pp. 283-297 Signal Processing, Elsevier Science Publishers B.V. Amsterdam, NL vol. 52 No. 3.

(56) References Cited

OTHER PUBLICATIONS

Bergdahl et al., "Studies on Coagulation and the Development of an Automatic Computerized Bipolar Coagulator" Journal of Neurosurgery 75:1, (Jul. 1991) pp. 148-151.
Cosman et al., "Theoretical Aspects of Radiofrequency Lesions in the Dorsal Root Entry Zone" Neurosurgery 15:(1984) pp. 945-950.
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
Medtrex Brochure—Total Control at Full Speed, "The O.R. Pro 300" 1 p. Sep. 1998.
Valleylab Brochure "Valleylab Electroshield Monitoring System" 2 pp. Nov. 1995.
International Search Report EP 98300964.8 dated Dec. 4, 2000.
International Search Report EP 04009964 dated Jul. 13, 2004.
International Search Report EP 04011375 dated Sep. 10, 2004.
International Search Report EP 04015981.6 dated Sep. 29, 2004.
International Search Report EP04707738 dated Jul. 4, 2007.
International Search Report EP 05002769.7 dated Jun. 9, 2006.
International Search Report EP 05014156.3 dated Dec. 28, 2005.
International Search Report EP 05021944.3 dated Jan. 18, 2006.
International Search Report EP 05022350.2 dated Jan. 18, 2006.
International Search Report EP 06000708.5 dated Apr. 21, 2006.
International Search Report—extended EP 06000708.5 dated Aug. 22, 2006.
International Search Report EP 06006717.0 dated Aug. 7, 2006.
International Search Report EP 06010499.9 dated Jan. 29, 2008.
International Search Report EP 06022028.2 dated Feb. 5, 2007.
International Search Report EP 06025700.3 dated Apr. 12, 2007.
International Search Report EP 07001481.6 dated Apr. 23, 2007.
International Search Report EP 07001485.7 dated May 15, 2007.
International Search Report EP 07001489.9 dated Dec. 20, 2007.
International Search Report EP 07001491 dated Jun. 6, 2007.
International Search Report EP 07001527.6 dated May 9, 2007.
International Search Report EP 07004355.9 dated May 21, 2007.
International Search Report EP 07008207.8 dated Sep. 13, 2007.
International Search Report EP 07009322.4 dated Jan. 14, 2008.
International Search Report EP 07010673.7 dated Sep. 24, 2007.
International Search Report EP 07015601.3 dated Jan. 4, 2008.
International Search Report EP 07015602.1 dated Dec. 20, 2007.
International Search Report EP 07019174.7 dated Jan. 29, 2008.
International Search Report EP08004667.5 dated Jun. 3, 2008.
International Search Report EP08006733.3 dated Jul. 28, 2008.
International Search Report EP08012503 dated Sep. 19, 2008.
International Search Report EP08013605 dated Nov. 17, 2008.
International Search Report EP08015601.1 dated Dec. 5, 2008.
International Search Report EP08016540.0 dated Feb. 25, 2009.
International Search Report EP08155780 dated Jan. 19, 2009.
International Search Report EP08166208.2 dated Dec. 1, 2008.
International Search Report EP09003678.1 dated Aug. 7, 2009.
International Search Report EP09005160.8 dated Aug. 27, 2009.
International Search Report EP09164754.5 dated Aug. 21, 2009.
International Search Report PCT/US03/33711 dated Jul. 16, 2004.
International Search Report PCT/US03/33832 dated Jun. 17, 2004.
International Search Report PCT/US03/37110 dated Jul. 25, 2005.
International Search Report PCT/US03/37310 dated Aug. 13, 2004.
International Search Report PCT/US04/02961 dated Aug. 2, 2005.
International Search Report PCT/US04/13443 dated Dec. 10, 2004.
International Search Report PCT/US09/46870 dated Jul. 21, 2009.

SYSTEM AND METHOD FOR POWER SUPPLY NOISE REDUCTION

CROSS-REFERENCE TO RELATED APPLICATIONS

This application claims priority as a divisional application to U.S. patent application Ser. No. 12/556,770, filed Sep. 10, 2009, the contents of which are incorporated herein by reference.

BACKGROUND

1. Technical Field

The present disclosure relates to an electrosurgical system and method and, more particularly, to pulse sequencing to minimize current draw on a shared power supply.

2. Background of Related Art

Energy-based tissue treatment is well known in the art. Various types of energy (e.g., electrical, ohmic, resistive, ultrasonic, microwave, cryogenic, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In bipolar electrosurgery, one of the electrodes of the hand-held instrument functions as the active electrode and the other as the return electrode. The return electrode is placed in close proximity to the active electrode such that an electrical circuit is formed between the two electrodes (e.g., electrosurgical forceps). In this manner, the applied electrical current is limited to the body tissue positioned between the electrodes.

Typically, multiple isolated power supplies are connected to the active terminals of the electrosurgical generator to power analog circuits associated with components connected to the electrosurgical generator (e.g., bipolar instruments, monopolar instruments, footswitches, etc.). For example, analog circuits configured to detect connected components and/or switching thereof may be included within the generator or within the connected components. Often, these isolated power supplies share the same low voltage power source. This is problematic when multiple supplies draw power from the shared power source substantially simultaneously, thereby maximizing the peak current draw on the shared power source. For example, the combined primary currents generated by certain isolated power supplies activated substantially simultaneously may be large enough to cause a decrease in output of the shared power source due to its output impedance or internal resistance. This decrease in output may cause output noise on the analog circuits drawing power therefrom, if those analog circuits do not have adequate power supply rejection bandwidth at the switching frequency of the isolated power supply to which they are connected.

SUMMARY

According to an embodiment of the present disclosure, a method for minimizing current draw on a power source for an electrosurgical system includes the step of generating a first pulse signal from a master device to electrically cooperate with a first floating power supply configured to create an electrical connection between one or more first loads and a power supply. The method also includes the step of triggering an ensuing pulse signal from a slave device based on the first pulse signal to electrically cooperate with a subsequent floating power supply configured to create an electrical connection between one or more subsequent loads and the power supply.

According to another embodiment of the present disclosure, a method for minimizing current draw on a power source for an electrosurgical system includes the steps of generating a first pulse signal and activating a first floating power supply based on the first pulse signal. The first floating power supply is configured to deliver power from a power source to one or more first loads. The method also includes the steps of generating a second pulse signal based on the first pulse signal and activating a second floating power supply based on the second pulse signal. The second floating power supply is configured to deliver power from the power source to one or more second loads. The method also includes the steps of generating an ensuing pulse signal based on a previously generated pulse signal and activating a subsequent floating power supply based on the ensuing pulse signal. The subsequent floating power supply is configured to deliver power from the power source to one or more additional loads.

According to another embodiment of the present disclosure, an electrosurgical system includes an electrosurgical generator adapted to supply electrosurgical energy to tissue and a power source operably coupled to the electrosurgical generator and configured to deliver power to one or more loads connected to the electrosurgical generator. The system also includes a master device configured to generate an initial pulse signal. The initial pulse signal electrically cooperates with a first floating power supply configured to create an electrical connection between one or more first loads and the power source. A plurality of slave devices are connected in series to the master device. A first slave device is configured to generate a subsequent pulse signal based on the initial pulse signal. The subsequent pulse signal electrically cooperates with a second floating power supply configured to create an electrical connection between one or more second loads and the power source. The subsequent pulse signal is configured to cause an ensuing slave device to generate an additional pulse signal. The additional pulse signal electrically cooperates with a corresponding floating power supply configured to create an electrical connection between at least one additional load and the power source.

BRIEF DESCRIPTION OF THE DRAWINGS

Various embodiments of the present disclosure are described herein with reference to the drawings wherein.

DETAILED DESCRIPTION

Particular embodiments of the present disclosure are described hereinbelow with reference to the accompanying drawings. In the following description, well-known functions or constructions are not described in detail to avoid obscuring the present disclosure in unnecessary detail.

The generator according to the present disclosure can perform monopolar and bipolar electrosurgical procedures, including vessel sealing procedures. The generator may include a plurality of outputs for interfacing with various electrosurgical instruments (e.g., a monopolar active electrode, return electrode, bipolar electrosurgical forceps, footswitch, etc.). Further, the generator includes electronic circuitry configured for generating radio frequency power specifically suited for various electrosurgical modes (e.g., cutting, blending, division, etc.) and procedures (e.g., monopolar, bipolar, vessel sealing).

Figure 1A:
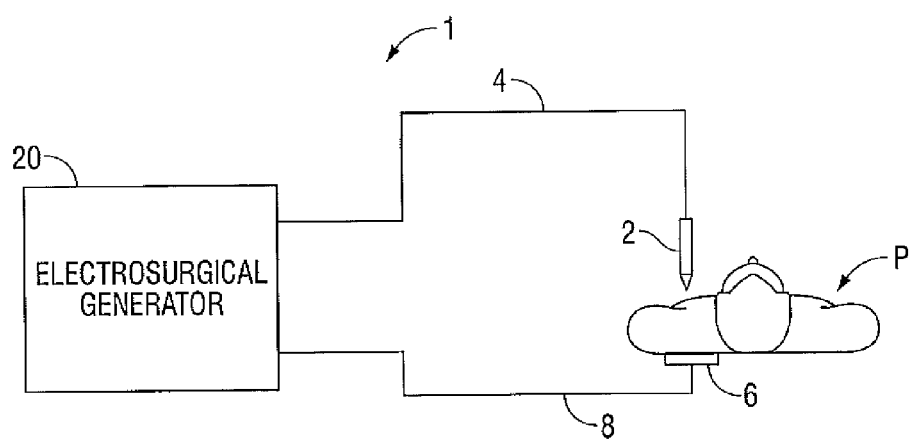
FIG. 1A is a schematic block diagram of a monopolar electrosurgical system in accordance with an embodiment of the present disclosure.

FIG. 1A is a schematic illustration of a monopolar electrosurgical system according to one embodiment of the present disclosure. The system includes an electrosurgical instrument 2 (e.g., monopolar) having one or more electrodes for treating tissue of a patient P (e.g., electrosurgical cutting, ablation, etc.). More particularly, electrosurgical RF energy is supplied to the instrument 2 by a generator 20 via a supply line 4, which is connected to any one of a plurality of active terminals 30a, 30b, 30c, . . . 30m (see FIG. 2) of the generator 20, allowing the instrument 2 to coagulate, seal, ablate and/or otherwise treat tissue. The energy is returned to the generator 20 through a return electrode 6 via a return line 8 at a return terminal 32 (see FIG. 2) of the generator 20. The active terminals 30a, 30b, 30c, . . . 30m and the return terminal 32 are connectors configured to interface with plugs (not explicitly shown) of the instrument 2 and the return electrode 6, which are disposed at the ends of the supply line 4 and the return line 8, respectively.

Figure 1B:
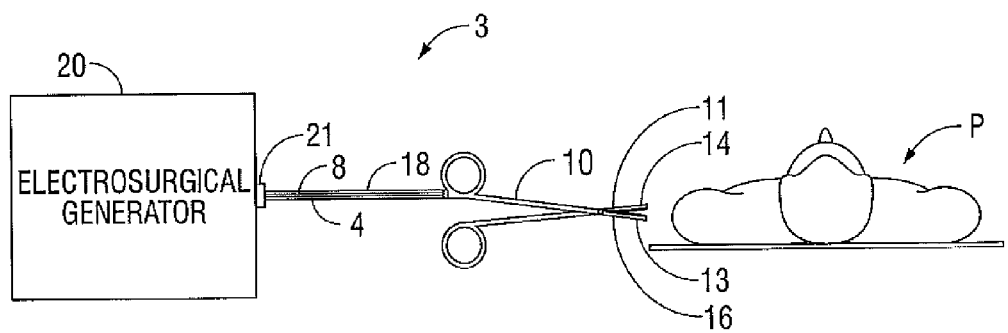
FIG. 1B is a schematic block diagram of a bipolar electrosurgical system in accordance with an embodiment of the present disclosure.

FIG. 1B is a schematic illustration of a bipolar electrosurgical system according to the present disclosure. The system includes a bipolar electrosurgical forceps 10 having one or more electrodes for treating tissue of a patient P. The electrosurgical forceps 10 includes opposing jaw members 11 and 13 having an active electrode 14 and a return electrode 16, respectively, disposed therein. The active electrode 14 and the return electrode 16 are connected to the generator 20 through cable 18, which includes the supply and return lines 4, 8 coupled to the active terminals 30a, 30b, 30c, . . . 30m and return terminal 32, respectively (see FIG. 2). The electrosurgical forceps 10 is coupled to the generator 20 at a connector 21 having connections to the active terminals 30a, 30b, 30c, . . . 30m and return terminal 32 (e.g., pins) via a plug disposed at the end of the cable 18, wherein the plug includes contacts from the supply and return lines 4, 8.

The generator 20 includes suitable input controls (e.g., buttons, activators, switches, touch screen, etc.) for controlling the generator 20. In addition, the generator 20 may include one or more display screens for providing the user with variety of output information (e.g., intensity settings, treatment complete indicators, etc.). The controls allow the user to adjust power of the RF energy, waveform parameters (e.g., crest factor, duty cycle, etc.), and other parameters to achieve the desired waveform suitable for a particular task (e.g., coagulating, tissue sealing, intensity setting, etc.).

Figure 2:
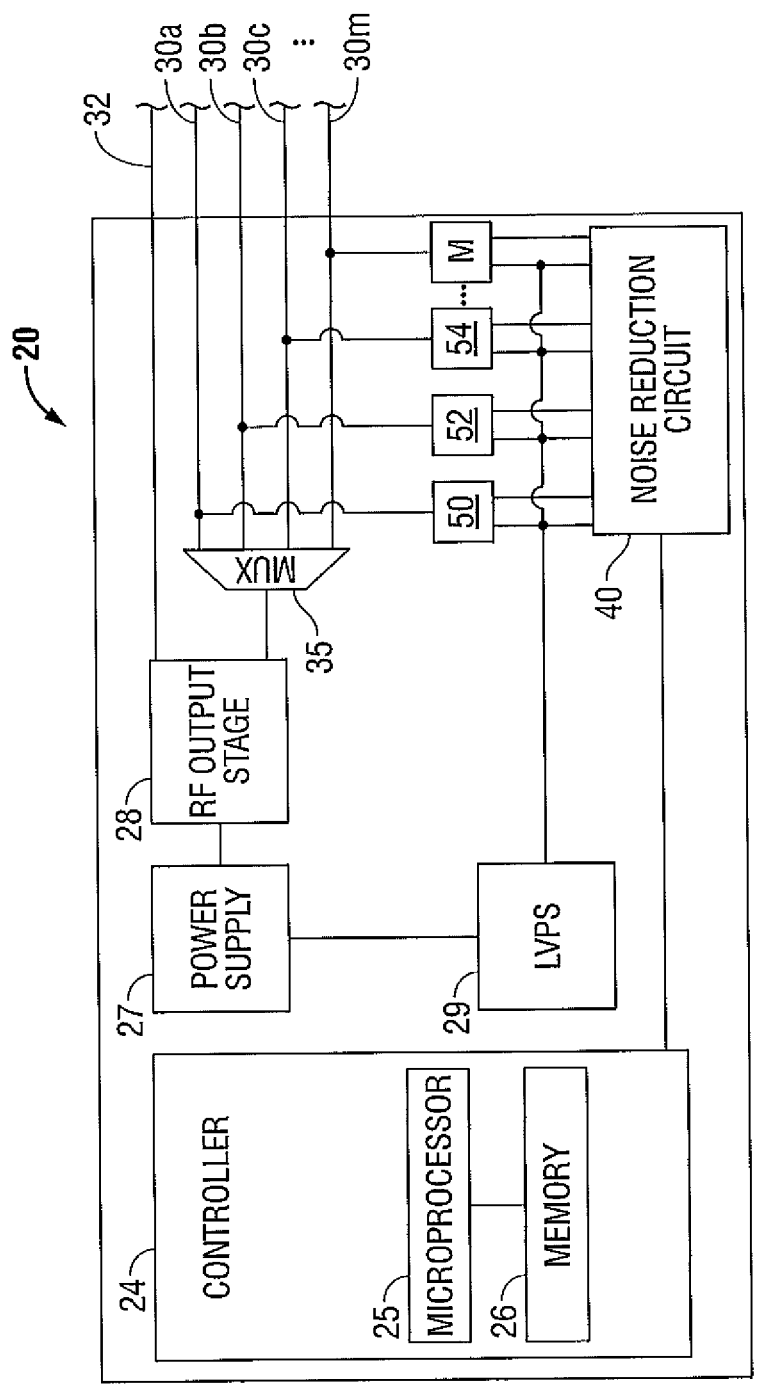
FIG. 2 is a schematic block diagram of a generator in accordance with an embodiment of the present disclosure.

FIG. 2 shows a schematic block diagram of the generator 20 having a controller 24, a DC power supply 27, and an RF output stage 28. The power supply 27 is connected to a conventional AC source (e.g., electrical wall outlet) and includes a low voltage power supply 29 ("LVPS") and a high voltage power supply (not explicitly shown). The high voltage power supply provides high voltage DC power to an RF output stage 28, which then converts high voltage DC power into RF energy. RF output stage 28 delivers the RF energy to the plurality of active terminals 30a, 30b, 30c, . . . 30m separately through a single-input multiple output multiplexer 35. The energy is returned thereto via the return terminal 32. The LVPS 29 provides power to various components of the generator (e.g., input controls, displays, etc.), as will be discussed in further detail below.

The generator 20 may include a plurality of connectors to accommodate various types of electrosurgical instruments (e.g., instrument 2, electrosurgical forceps 10, etc.). Further, the generator 20 may be configured to operate in a variety of modes such as ablation, monopolar and bipolar cutting coagulation, etc. The generator 20 may also include a switching mechanism (e.g., relays) to switch the supply of RF energy between the connectors, such that, for example, when the instrument 2 is connected to the generator 20, only the monopolar plug receives RF energy.

The controller 24 includes a microprocessor 25 operably connected to a memory 26, which may be volatile type memory (e.g., RAM) and/or non-volatile type memory (e.g., flash media, disk media, etc.). The microprocessor 25 includes an output port that is operably connected to the power supply 27 and/or RF output stage 28 allowing the microprocessor 25 to control the output of the generator 20 according to either open and/or closed control loop schemes. Those skilled in the art will appreciate that the microprocessor 25 may be substituted by any logic processor (e.g., control circuit) adapted to perform the calculations discussed herein.

A noise reduction circuit 40 is operably coupled to the controller 24 and is configured to control power drawn on the LVPS 29 by one or more isolated floating power supplies 50, 52, 54, . . . "m". Each supply 50, 52, 54 . . . "m" may be an isolated power converter such as, for example, a so-called "flyback converter" electrically connected to the LVPS 29 and configured to power a load 51, 53, 55, . . . "x", respectively (see FIG. 3). Load 51, 53, 55, . . . "x" may be, for example, one or more low-signal-level analog circuits configured to detect switching of a handset (e.g., instrument 2, forceps 10, etc.) connected to one of the plurality of connectors of generator 20 and/or drawing energy from RF output stage 28 via any one of active terminals 30a, 30b, 30e, . . . 30m. As shown in the illustrated embodiment of FIG. 2, supplies 50, 52, 54, . . . "in" float at corresponding active terminals 30a, 30b, 30c, . . . 30m and share the same low voltage power source (e.g., LVPS 29). This is problematic when multiple supplies draw power from LVPS 29 substantially simultaneously, thereby maximizing the peak current draw from LVPS 29. In the scenario wherein supplies 50, 52, 54, . . . "m" are embodied as flyback converters, for example, the combined primary currents generated by flyback converters activated substantially simultaneously may be large enough to cause a drop in output of LVPS 29 due to the output impedance or internal resistance of LVPS 29. This drop in output of LVPS 29 may cause output noise on circuits (e.g., load 51, 53, 55, . . . "x") drawing power therefrom especially if those circuits do not have adequate power supply rejection bandwidth at the switching frequency of the power supply (e.g., supplies 50, 52, 54, . . . "m").

Figure 3:
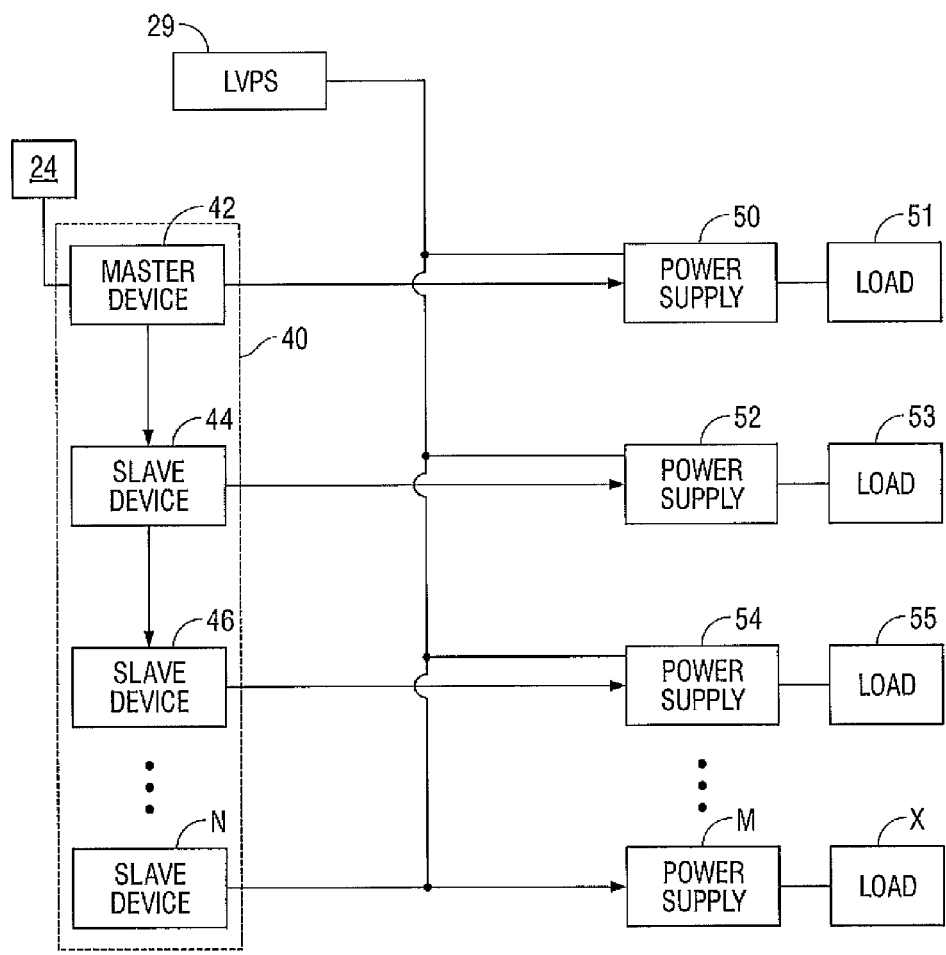
FIG. 3 is a schematic block diagram of specific components of the generator of FIG. 2 in accordance with an embodiment of the present disclosure.

FIG. 3 shows a circuit schematic of the noise reduction circuit 40. Noise reduction circuit 40 includes a master device 42 and one or more slave devices 44, 46, . . . "n" connected in series therewith. Master device 42 and each of slave devices 44, 46, . . . "n" may be an integrated circuit such as, for example, a 555 timer having an RC network (not shown). In a so-called "monostable mode," 555 timers act as a "one-shot" pulse generator. The one-shot pulse initiates when the 555 timer receives a trigger signal (e.g., a one-shot pulse from a previous 555 timer). Upon receiving the trigger signal, the 555 timer outputs the one-shot pulse as a function of a time constant of the RC network. In a scenario wherein a 555 timer is sequenced or chained to ensuing 555 timers, this configuration has the effect of each ensuing 555 timer receiving, as input, a one-shot pulse generated by the previous 555 timer to trigger a one-shot pulse output as a function of the time constant. That is, for a given 555 timer, a time delay exists between the reception of a trigger pulse and an output pulse as dictated by the time constant of the RC network of that 555 timer. In this manner, the one-shot pulses generated by a chain of 555 timers are sequenced or chained in accordance with the time constant of the RC network for each 555 timer, thereby minimizing the peak current draw on the common power source (e.g., LVPS 29) to which they are connected.

With this scenario in mind, master device 42 is configured to generate a pulse signal (e.g., a master switching frequency) that operates to cause a load 51 connected to supply 50 to draw power from LVPS 29. The pulse signal generated by master device 42 triggers slave device 44 to subsequently generate a one-shot pulse, as discussed above with respect to monostable mode of operation for a 555 timer, that operates to cause a load 53 connected to supply 52, to draw power from LVPS 29. Further, the one-shot pulse generated by slave device 44 triggers ensuing slave device 46 to generate a one-shot pulse that operates to cause a load 55 connected to supply 54 to draw power from LVPS 29. Further, the one-shot pulse generated by slave device 46 triggers an ensuing slave device "n" to operate in like manner to the previous slave devices 44 and 46. That is, each ensuing slave device "n" connected in series with master device 42 is configured to receive a triggering one-shot pulse from a previous slave device "n–1" and, in turn, subsequently generate a one-shot pulse to cause a load "x" connected to an ensuing supply "in" to draw power from LVPS 29. In this manner, a sequenced or chained activation of supplies 50, 52, 54, . . . "n" (as opposed to substantially simultaneous activation thereof), minimizes the peak current draw on LVPS 29. This, in turn, minimizes output noise on loads 51, 53, 55, . . . "x" connected to supplies 50, 52, 54, . . . "n", respectively, as discussed hereinabove.

In other embodiments, each of slave devices 44, 46, . . . "n" may be a so-called "tapped delay line" configured to simulate an echo of a source signal generated by master device 42 to sequentially activate supplies 50, 52, 54, . . . "n".

Figure 4:
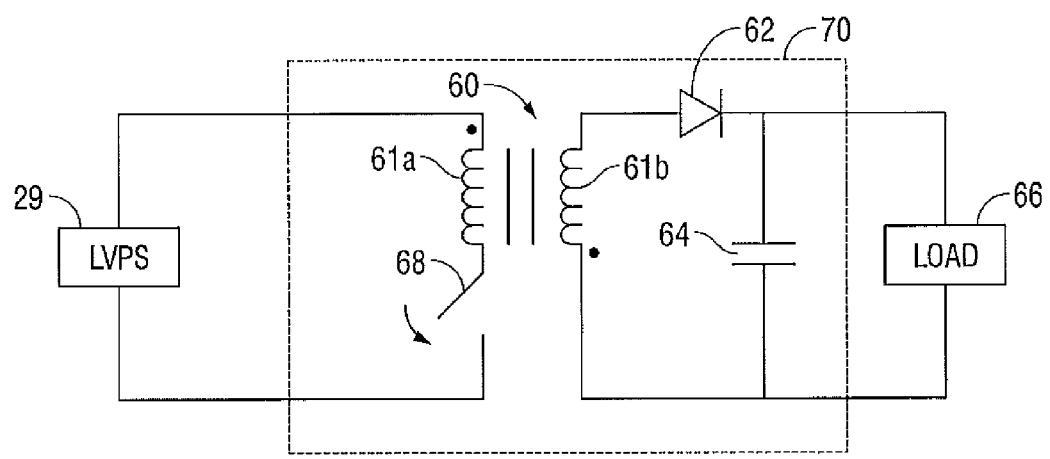
FIG. 4 is a circuit diagram of a power supply according to an embodiment of the present disclosure.

By way of example, FIG. 4 illustrates a circuit diagram of a flyback converter 70 including a transformer 60 having a primary winding 61a and a secondary winding 61b. Primary winding 61a is connected in series with a switching component 68 (e.g., a transistor). Secondary winding 61b is connected in series with a diode 62, both of which are in parallel with a capacitor 64 and a load 66 (e.g., analog circuit). In operation, a pulse signal generated by master device 42, or any one of ensuing slave devices 42, 44, 46, . . . "n", closes or turns on switching component 68. When switching component 68 is on or closed, the primary coil 61a of inductor 60 is directly connected to the LVPS 29, resulting in an increase of magnetic flux in the transformer 60 and a positive voltage across the secondary winding 61b of transformer 60. This positive voltage across the secondary winding 61b causes diode 62 to be forward-biased and, as a result, the energy stored in transformer 60 is transferred to the capacitor 64 and/or the load 66. When the switching component 68 is off or open, as shown in FIG. 4, the transformer GO induces a negative voltage across secondary winding 61b sufficient to cause diode 62 to be reverse-biased (or blocked) and, as a result, the capacitor 64 supplies energy to the load 66.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An electrosurgical system, comprising:
an electrosurgical generator adapted to supply electrosurgical energy to tissue;
a power source operably coupled to the electrosurgical generator and configured to deliver power to at least one load connected to the electrosurgical generator;
a master device configured to generate an initial pulse signal, the initial pulse signal electrically cooperating with a first floating power supply configured to create an electrical connection between at least one first load and the power source; and
a plurality of slave devices connected in series to the master device, wherein a first slave device of the plurality of slave devices is configured to generate a subsequent pulse signal based on the initial pulse signal, the subsequent pulse signal electrically cooperating with a second floating power supply configured to create an electrical connection between at least one second load and the power source, the subsequent pulse signal configured to cause an ensuing slave device of the plurality of slave devices to generate an additional pulse signal, the additional pulse signal electrically cooperating with a corresponding floating power supply configured to create an electrical connection between at least one additional load and the power source.

2. The electrosurgical system according to claim 1, wherein at least one of the master device and the plurality of slave devices is a 555 timer configured to generate a one-shot pulse signal.

3. The electrosurgical system according to claim 1, wherein at least one of the first, the second, and the corresponding floating power supplies is a flyback converter.

4. The electrosurgical system according to claim 1, wherein the power source is a low voltage power supply.

5. The electrosurgical system according to claim 1, wherein at least one of the initial pulse signal, the subsequent pulse signal, or the additional pulse signal is a one-shot signal.

6. The electrosurgical system according to claim 1, wherein the electrosurgical system is configured to sequence the initial pulse signal and the subsequent pulse signal, such that the electrical connection between the at least one first load and the power source is created substantially prior to the electrical connection between the at least one second load or the at least one additional load and the power source.

7. The electrosurgical system according to claim 1, wherein the electrosurgical system is configured to generate a time delay between each initial, second, and additional pulse signal, such that the electrical connection between the at least one first load and the power source is created substantially prior to the electrical connection between the at least one second load or the at least one additional load and the power source.

8. The electrosurgical system according to claim 7, wherein the time delay is a function of a time constant of an RC network.

9. The electrosurgical system according to claim 1, further comprising a 555 timer configured to generate at least one of the initial pulse signal and the subsequent pulse signal.

* * * * *